US009565854B2

(12) United States Patent
Woods (10) Patent No.: US 9,565,854 B2
(45) Date of Patent: *Feb. 14, 2017

(54) SYSTEMS AND METHODS FOR CRYOPRESERVATION OF CELLS

(71) Applicant: Cook General Biotechnology LLC, Indianapolis, IN (US)

(72) Inventor: Erik John Woods, Indianapolis, IN (US)

(73) Assignee: Cook General Biotechnology LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/187,418

(22) Filed: Feb. 24, 2014

(65) Prior Publication Data

US 2014/0170634 A1    Jun. 19, 2014

Related U.S. Application Data

(63) Continuation of application No. 12/711,929, filed on Feb. 24, 2010, now Pat. No. 8,709,797, which is a continuation-in-part of application No. 12/337,237, filed on Dec. 17, 2008, now Pat. No. 8,222,027, which is a continuation-in-part of application No.
(Continued)

(51) Int. Cl.
  *C12M 1/12*    (2006.01)
  *C12M 3/06*    (2006.01)
  *A01N 1/02*    (2006.01)

(52) U.S. Cl.
  CPC ............. *A01N 1/0257* (2013.01); *A01N 1/02* (2013.01); *A01N 1/0231* (2013.01); *A01N 1/0263* (2013.01); *A01N 1/0268* (2013.01); *A01N 1/0284* (2013.01)

(58) Field of Classification Search
  CPC ...... A01N 1/02; A01N 1/0257; A01N 1/0263; A01N 1/0268; A01N 1/0284
  See application file for complete search history.

(56) References Cited

U.S. PATENT DOCUMENTS 2,653,606 A    9/1953   Ryan
3,870,042 A    3/1975   Viguier
(Continued)

FOREIGN PATENT DOCUMENTS

CN    201222947 Y    4/2009
EP    0 246 824 A2    3/1994
(Continued)

OTHER PUBLICATIONS

E Moce et al: "Cholesterol-loaded cyclodextrins added to fresh bull ejaculates improve sperm cryosurvival" Journal of Animal Science, vol. 84, No. 4, Apr. 1, 2006 pp. 826-833, XP55041886.
(Continued)

*Primary Examiner* — William H Beisner (57) ABSTRACT

A fluid sample vessel includes inlet and vent tube fittings formed at one end of a container with an opposite open end closed by a needle septum. A support cap is removably engaged to the container to support the container and protect terminal ends of inlet and vent tubular branches coupled to the fittings. The support cap includes a pair of opposite legs with outwardly directed tabs for mounting within a centrifuge while supporting the cryopreservation container.

22 Claims, 7 Drawing Sheets

Related U.S. Application Data

11/765,000, filed on Jun. 19, 2007, now Pat. No. 7,939,316, which is a continuation-in-part of application No. PCT/US2007/071545, filed on Jun. 19, 2007.

(60) Provisional application No. 60/814,982, filed on Jun. 20, 2006.

(56) References Cited

U.S. PATENT DOCUMENTS

| | | | |
|---|---|---|---|
| 4,262,494 | A | 4/1981 | Karow, Jr. |
| 4,317,525 | A | 3/1982 | Schuessler et al. |
| 4,338,933 | A | 7/1982 | Bayard et al. |
| 4,364,903 | A | 12/1982 | Bittings |
| 4,626,246 | A * | 12/1986 | Verkade ............... A61M 25/02 128/877 |
| 4,928,493 | A | 5/1990 | Gilbertson, et al. |
| 4,995,386 | A | 2/1991 | Ng |
| 5,190,880 | A | 3/1993 | Cassou |
| 5,460,625 | A | 10/1995 | Johnson |
| 5,897,840 | A | 4/1999 | Owens et al. |
| 6,592,613 | B1 | 7/2003 | Ishida et al. |
| 7,598,724 | B2 | 10/2009 | Howell et al. |
| 7,939,316 | B2 * | 5/2011 | Woods et al. ............. 435/307.1 |
| 8,222,027 | B2 * | 7/2012 | Woods et al. ............. 435/307.1 |
| 8,709,797 | B2 * | 4/2014 | Woods ................... 435/307.1 |
| 8,936,905 | B2 * | 1/2015 | Woods et al. ................. 435/2 |
| 2004/0097862 | A1 | 5/2004 | Lampeter et al. |
| 2007/0275459 | A1 | 11/2007 | Terashima et al. |
| 2008/0135559 | A1 | 6/2008 | Byrd |
| 2009/0148934 | A1 | 6/2009 | Woods et al. |
| 2010/0196873 | A1 | 8/2010 | Woods et al. |

FOREIGN PATENT DOCUMENTS

| | | |
|---|---|---|
| JP | H05-502662 | 5/1993 |
| JP | H05-502663 | 5/1993 |
| JP | H05-502664 | 5/1993 |
| JP | 2002-523774 | 7/2002 |
| JP | 2004-236527 | 8/2004 |
| WO | WO 91/01636 A1 | 2/1991 |
| WO | WO 91/01637 A1 | 2/1991 |
| WO | WO 91/01992 A1 | 2/1991 |
| WO | WO 00/13003 | 3/2000 |
| WO | WO 01/50852 | 7/2001 |
| WO | WO 2005/035737 A1 | 4/2005 |

OTHER PUBLICATIONS

English translation of Office Action fo Japanese Patent Application No. 2009-516675 corresponding to PCT/US2007/071545, Sep. 20, 2011.

PCT Search report and opinion for PCT/US2007/071545, May 21, 2008, pp. 3, 7-8.

Written Opinion for related Singapore Patent Application No. SG200809427-8, Australian Patent Office, Oct. 20, 2009.

JP 2004-236527, English Abstract.

* cited by examiner

SYSTEMS AND METHODS FOR CRYOPRESERVATION OF CELLS

CROSS-REFERENCE TO RELATED APPLICATIONS

The present application is a continuation and claims priority of U.S. application Ser. No. 12/711,929, filed on Feb. 24, 2010 and which is a continuation-in-part and claims priority to U.S. application Ser. No. 12/337,237, filed on Dec. 17, 2008, now U.S. Pat. No. 8,222,027, issued Jul. 17, 2012, and which is a continuation-in-part and claims priority to U.S. application Ser. No. 11/765,000, now U.S. Pat. No. 7,939,316, issued May 10, 2011, and to co-pending international application No. PCT/US2007/071545, both of which were filed on Jun. 19, 2007, and both of which claim priority to provisional application No. 60/814,982, entitled "Systems and Methods for Cryopreservation of Cells", which was filed on Jun. 20, 2006, all of which are incorporated herein by reference.

BACKGROUND OF THE INVENTION

The present invention concerns storage methods and associated devices for cryopreservation of cells, such as mammalian cells, and tissue samples/specimen.

Cells and tissues are frequently cryopreserved to temporally extend their viability and usefulness in biomedical applications. The process of cryopreservation involves, in part, placing cells into aqueous solutions containing electrolytes and chemical compounds that protect the cells during the freezing process (cryoprotectants). Such cryoprotectants are often small molecular weight molecules such as glycerol, propylene glycol, ethylene glycol or dimethyl sulfoxide (DMSO).

As these solutions are cooled to temperatures slightly below their freezing point, the solution remains in the liquid state. This condition in which the solution remains liquid below its phase transition temperature is termed supercooling. As the aqueous solutions are cooled further below their freezing point, the extent of supercooling increases. In the absence of intervention, the water molecules in the solution will, at a point usually no more than 15.degree. C. below the freezing point, spontaneously crystallize, and pure water will precipitate as ice.

During this transition from the liquid to the solid state, the solution moves from a higher to a lower free energy state, resulting in an exothermic reaction. The heat produced during this phase transition causes a transient warming of the sample during which the sample temperature increases. Meanwhile the surrounding environment (e.g. the device in which the sample is being cryopreserved) either remains at a constant temperature or continues to cool (depending upon the cooling approach used). Subsequently, as the heat in the sample dissipates, the thermal dis-equilibrium between the sample and cooling device created during this event causes the sample to undergo a rapid cooling rate to re-establish thermal equilibrium. In many cases this rapid cooling rate causes the formation of intracellular ice, which usually results in cell death. This formation of intracellular ice is typically dependent upon the mass of the sample, the heat transfer properties of the sample container, the cooling protocol used and the fundamental cryobiological properties of the cells.

The relationship between the frozen state and living systems has been fascinating mankind for years. As early as 1683, Robert Boyle observed that some fish and frogs could survive sub-freezing temperatures for short periods of time if a fraction of their body water remained unfrozen. Artificially induced cryopreservation was first observed in 1948 by Polge, Smith, and Parkes by the serendipitous discovery of the cryo-protective properties of glycerol for fowl and bull semen and, subsequently, for red blood cells. In more recent times, scientists interested in the natural phenomena and biomedical applications associated with freezing biological systems have begun to investigate the fundamental processes governing the relationship. To begin with, it is well known that decreased temperature results in the suppression of metabolic activity and, thus, in a reduction of the rate at which deterioration of an unnourished biological system would occur. The freezing process, however, is not as benign as one might assume; it generally induces extreme variations in chemical, thermal, and electrical properties that could be expected to alter intracellular organelles, cellular membranes and the delicate cell-cell interaction systems associated with tissues and organs. Indeed, given the extreme complexity of even the simplest biological cells, it is therefore remarkable that a reversible state of suspended animation by freezing is possible at all.

Since that first discovery of the cryoprotective effects of glycerol and the subsequent discovery of the widely applicable permeating cryoprotectant dimethyl sulfoxide (DMSO)), many investigators have attempted the preservation of cells or tissues, mostly through empirical methods. Most cell suspension cryopreservation protocols have been established using molar concentrations of permeating cryoprotective additives to enable freezing survival. By using these artificial cryoprotectants, much flexibility has been added to the cryopreservation process. For example, human red blood cells need to be cooled at a rate of around 1000.degree. C./min. for optimal survival without the addition of a cryoprotective agent (CPA). In the presence of 3.3M (30%) glycerol, however, survival of this cell type remains around 90% over a 2-3 log range in cooling rates. As can be expected, the higher the CPA concentration, the greater the likelihood of osmotic damage during the addition/removal of the substance, and consequently the greater care that is necessary in these processes.

During any cryopreservation process, the solutions involved will supercool below their freezing point until they find a random nucleation site for crystal formation. When cryopreserving by a freeze-thaw method, ice formation in the extracellular medium should be deliberately initiated by seeding at low degrees of supercooling. If ice formation is not induced by seeding, ice will form spontaneously when the solution is cooled sufficiently far below its equilibrium freezing point. Because this process is random in nature, ice formation will occur at random, unpredictable temperatures; consequently, sample survival rates will be highly variable between repeated trials with the same freezing protocol. Furthermore, the extremely rapid crystallization which results when ice forms in a highly supercooled solution causes damage to cells and tissues. Moreover, it has been shown that if extracellular ice formation is initiated at high degrees of supercooling, the probability of damaging intracellular ice formation is drastically increased. This phenomenon results from the delayed onset of freeze-induced cell dehydration, which results in increased retention of intracellular water, and thus higher likelihood of ice formation in the cell.

As noted above, during the transition from the liquid to the solid state, the solution moves from a higher to a lower free energy state which results in thermal disequilibrium between the sample that continues to warm and the cooling device that continues to cool. This disequilibrium ultimately results in a severe deviation from the cooling rate prescribed for the particular cell type, and the potential for cell damage during the process.

To prevent these potentially damaging situations from occurring, steps in the cryopreservation process often include interventions to introduce ice crystals in the extracellular solution near the solution freezing point. This process called "seeding" is typically performed by cooling the samples to near the solution freezing point, then touching the outside of the sample container with a metal device (e.g. forceps or a metal rod) precooled in a cryogenic fluid (e.g. liquid nitrogen). This seeding step produces ice crystals in the extracellular solution and provides a "template" upon which supercooled water molecules in the solution organize and produce further ice. However, seeding samples in this manner is time consuming and places the samples at risk in cases where they are temporarily removed from the cooling device for this procedure and because this method of seeding may inadvertently cause intracellular ice formation.

There is a need for a cryopreservation system that avoids the problems associated with the disequilibrium conditions described above. There is a further need for such a system that does not require the ancillary seeding step currently conducted to induce controlled ice crystal production. There is an additional need for a cryopreservation device that facilitates the solution to the above-noted problems. The needed cryopreservation device should also provide means to simplify its use in acquiring and storing cells and tissue to be cryopreserved.

SUMMARY OF THE INVENTION

These and other needs in the field of cryopreservation are met by several aspects of the present invention. In one aspect of the invention, an auto-nucleating device is provided for introduction into a cryopreservation vessel prior to freezing of a liquid contained therein. The device comprises an elongated hollow tube sized for introduction into the cryopreservation vessel and an ice-nucleating composition disposed within the hollow tube. Both ends of the tube are sealed, while at least one end is sealed with a membrane that is impermeable to the ice-nucleating composition but permeable to the liquid contained within the cryopreservation vessel. Preferably, both ends include the membrane to permit flow of the sample liquid into and through the device.

In the preferred embodiment, the ice-nucleating composition is a sterol, and most preferably cholesterol. The cholesterol may be a coating on the interior of the hollow tube or may be provided as a solid matrix within the tube.

In another aspect of the invention, cryopreservation vessels are provided that may be used with the auto-nucleating device. In one embodiment, the cryopreservation vessel comprises a flexible tubular body having one end initially open for the introduction of a liquid sample into the body and a closed port defined at an opposite end of the body. The port is adapted to be pierced by a needle for withdrawal of the liquid sample. The open end is heat sealed after the liquid sample ha been introduced into the vessel. The auto-nucleating device is affixed to the interior of the tubular body offset from the inlet so that it cannot be contacted by a needle piercing the closed port.

In another embodiment, the cryopreservation device comprises a container for receiving and storing a liquid sample, the container having an inlet fitting opening into the container and an adaptor mounted to the fitting. The adaptor has a first tubular branch and a second tubular branch, with the second tubular branch terminating in a tube engaging fitting. A septum closes the first tubular branch, in which the septum is adapted to be pierced by a needle. The cryopreservation device is further provided with a tube engaged at one end to the tube engaging fitting on the second tubular branch and a closure at the opposite end of the tube.

The closure for the second branch is initially a septum that may be pierced by a needle for introduction of the sample liquid into the vessel. The container may be initially at below-atmospheric pressure to enhance transfer of the sample liquid from a syringe into the vessel. Once the sample liquid has been transferred, the tube on the second branch is heat sealed and severed just above the tube engaging fitting to form a final closure for the second branch. The closed device may then be subject to a freezing and thawing protocol. After thawing a syringe may be used to withdraw the sample liquid through the septum in the first branch of the adaptor.

It is contemplated that the present invention will provide a simple and reproducible system for induction of ice and reduction of supercooling in many different cell freezing applications. The invention contemplates methods and devices for the controlled extracellular induction of ice crystals during cryopreservation of cells and tissues via the construction of solid-state matrix devices where ice nucleation will occur spontaneously.

The present invention poses several advantages over prior systems and methods. Currently, most methods of inducing controlled ice nucleation are cumbersome, difficult to reproduce, and are many times over-looked, despite the large body of literature pointing to the enhanced freeze-thaw survival of many cells and tissues when the technique is employed. To date, the most commonly used methods have ranged from simply touching the side of a vial or straw with a chilled (usually to −196.degree. C.) metal object or cotton swab, to elaborate devices designed to spay liquid nitrogen on a small area of the sample. However, even when performed under optimal conditions, mechanically seeding ice crystals in this manner can result in a failure to induce a large enough ice crystal to allow full propagation throughout the extracellular solution, or, in localized cell damage and loss due to the enormous cooling rates observed in the portion of the sample closest to where the metal object or liquid nitrogen spray is being directed on the container.

In one feature, a fluid sample device comprises a container for receiving and storing a liquid sample, the container formed by a one-piece elongated body. The body defines a hollow interior from an open end and is closed at an opposite end by an inlet tube fitting and a vent tube fitting opening to the hollow interior. In one aspect, the one-piece body further defines a wall extending into the hollow interior and disposed between the inlet and vent tube fittings. The open end of the container is closed by a needle septum. The device may further comprise an adaptor body mounted to the tube fittings, the adaptor body having an inlet tubular branch and a vent tubular branch, the vent tubular branch including a filter element disposed therein.

In a further aspect, a support cap is provided having a lower portion removably engagable to the container and an upper portion extending beyond the inlet and vent tube fittings at the opposite end of the container when the support cap is engaged to the container. The container may define at least two recesses in an outer surface thereof, while the lower portion of the support cap includes at least two resiliently deflectable elongated prongs, each having an inwardly directed tab configured to be removably received within a corresponding one of the recesses.

In one aspect, the upper portion of the support cap includes a cylindrical wall surrounding the inlet and vent tube fittings, and further includes interior walls flanking opposite sides of the inlet and vent tube fittings. In a further embodiment, the lower portion of the support cap includes two opposite elongated legs, each of the legs including an outwardly directed tab at a free end thereof. The elongated legs may be longer than the elongated prongs.

A method for using the device to obtain a liquid sample for analysis or for cryopreservation is contemplated comprising the initial steps of mounting an adaptor body on the tube fittings, the adaptor body having an inlet tubular branch and a vent tubular branch corresponding to the inlet and vent tube fittings and coupling the inlet tubular branch to a source of liquid. The method continues with introducing the liquid through the inlet tube fitting into the container while venting air within the container through the vent tube fitting and vent tubular branch, and then severing and sealing the inlet and vent tubular branches at a position to be within the upper portion of the support cap.

With the container completely closed, the support cap is mounted on the container. The combination is mounted within a centrifuge that is operated to centrifugally separating supernatant from the liquid with the supernatant directly exposed to the needle septum. Using a needle extending through the septum, the supernatant is drawn from within the container. The remaining liquid may then be cryopreserved, with or without the support cap mounted to the container.

DESCRIPTION OF THE ILLUSTRATED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
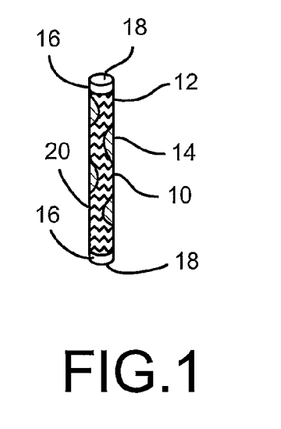
FIG. 1 is a view of an auto-nucleating device according to one embodiment of the present invention.

In one embodiment of the invention, an auto-nucleating device 10 is provided, as shown in FIG. 1, which involves the use of compositions capable of ice nucleation. In accordance with the present invention, an ice nucleating composition 20 is bound to the inner surface 14 of a hollow open tube 12. In a preferred embodiment, the tube is formed of plastic. A sufficient amount of the nucleating composition is introduced into the tube to form a solid matrix within the tube while permitting liquid flow through the tube.

In a preferred embodiment, the nucleating composition is crystalline cholesterol. The use of sterol compositions, and especially cholesterol, is known in other fields, such as in chill water systems, as shown in U.S. Pat. No. 4,928,493. In these other uses, powdered compositions are disposed within a container for exposure to water to assist in the formation of ice. As explained below, it was determined after experimentation that crystalline cholesterol was non-toxic to the sample cells and liquids being prepared for cryopreservation, such as blood, stem cell solutions and semen.

The ends 16 of the tube are sealed with a solution-permeable membrane 18. In particular, the membrane is permeable to the cryopreservation liquid and impermeable to cells or tissue to be preserved. It is important to maintain separation and prevent direct contact between the cells/tissue and the ice nucleating composition. The membranes at each end will also contain any cholesterol crystals that may dislodge from the tube and prevent the crystals from contaminating the surrounding liquid. It is also important that the membrane permit free flow of the cryopreservation liquid into the tube 12. The tube and the interstices in the solid matrix nucleating composition may also be initially filled with an isotonic buffer.

Figure 2:
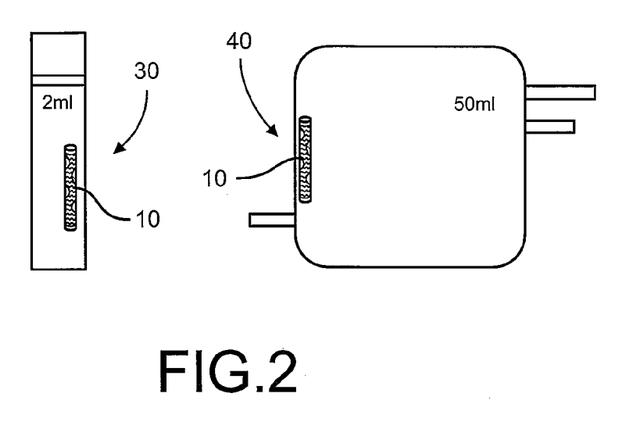
FIG. 2 is a view of known cryopreservation vessels incorporating the auto-nucleating device shown in FIG. 1.

This auto-nucleating device 10 is sized to be placed into a cryopreservation vessel such as a vial 30 or a blood bag 40, as shown in FIG. 2. The device may be free within the vessels or may be affixed to an interior surface. Since the device is intended as a nucleation site for ice formation, it does not need to be very large. In a specific embodiment, the tube 12 is 0.25 inches long and 0.0625 inches in diameter. The cryopreservation vessel may be filled with the particular specimen or sample, and a cryopreservation solution, where appropriate, as is known in the art, while the device 10 remains within the container. The container 30 or 40 is then subjected to a cryopreservation protocol. Since the cryopreservation liquid is in contact with the ice nucleating composition 20 within the device, ice will spontaneously form inside the tube 12 of the device 10 with little or no supercooling. Ice then continues to build off the tube into the surrounding solution, resulting in freezing of the cell suspension with little or no supercooling and minimal intracellular ice formation.

In one specific embodiment, a first experiment was designed to determine that cholesterol physically bound to the inside of cryo-storage vessels will induce ice nucleation. In this embodiment, the working sterol solution was prepared by adding 0.025 g of dry cholesterol to 3 ml of methanol. The resulting suspension was then placed into a 70.degree. C. dry bath and agitated intermittently until all solid sterol had dissolved. Commercially available vials were coated with 100.mu.l of the sterol solution and placed in the dry bath at 75.degree. C. to allow the methanol to evaporate, and to achieve cholesterol recrystallization and adhesion. Vials were then rinsed with 1 ml of PBS, 2-3 times, to remove any loose crystals.

Next, solutions of 6% glycerol (to replicate a typical sperm bank cryopreservation media) and 10% DMSO (to replicate a generalized cell-line cryopreservation system) were prepared in PBS and were evaluated by cooling at −5.degree. C./minute in a sterol coated vial and in a non-coated (control) vial. To achieve statistical power, 20 vials containing DMSO and 12 vials containing glycerol were evaluated. The temperature inside each vial was monitored using a thermocouple at one second intervals to allow resolution of the solution freezing point and release of the latent heat of fusion.

The results of this experiment indicated that in both DMSO and glycerol the freezing point was higher and the temperature change during heat of fusion (.DELTA.T) was reduced for vials coated with the sterol. These results are summarized in the following table:

| | FREEZING POINT | $\Delta T$ |
|---|---|---|
| Sterol Coated; DMSO | −4.56 ± 1.72° C. | 0.37 ± 1.29° C. |
| Non-Coated; DMSO | −10.61 ± 3.52° C. | 5.63 ± 4.36° C. |
| Sterol Coated; Glycerol | −2.97 ± 1.14° C. | 1.54 ± 1.47° C. |
| Non-Coated; Glycerol | −9.33 ± 4.01° C. | 7.24 ± 3.61° C. |

In this experiment, some sloughing or chipping of the crystals (and some degree of dissolution in the DMSO samples) was also observed, resulting in solution contamination (possibly due in part to unavoidable physical manipulation of the containers and the solutions). In order to address this problem, one embodiment of an auto-nucleating device 10 was provided in which a 0.25 inch hollow tube was coated on the interior with 100.mu.l of sterol solution and allowed to dry for 48 hours. One end of the tube was sealed with a permeable cotton plug, while the other end of the tube was attached to the inside of a vial lid using an epoxy resin and allowed to dry for 14-24 hours. The stent was designed to keep the bound cholesterol in a sequestered environment while still allowing solution (but not cells) in to make contact.

In a second experiment, human semen was cryopreserved using this auto-nucleating device 10 and was specifically analyzed to determine whether the samples cryopreserved in accordance with the present invention had a higher post-thaw viability than semen frozen using standard configuration vials. In this experiment, discarded human semen samples (20 samples from 4 donors) were obtained and were placed into a humidified 37.degree. C. incubator (5% $CO_2$, 95% air) for 30-60 minutes until liquefied. Once liquefied, the samples were adjusted to 5 ml using isotonic PBS (equilibrated to 37.degree. C.) and evaluated using a computer assisted semen analysis device to measure and record overall initial count and motility. The samples were then equilibrated to 6% glycerol in a TEST egg yolk buffer through a step-wise addition procedure. Following equilibration, each sample was divided into three 1.5 ml aliquots and deposited into (1) a vial containing the device 10; (2) a standard vial to be manually seeded (positive control); and (3) a standard vial which was to receive no seeding (negative control).

All samples were placed into a controlled-rate freezer and cooled from 22.degree. C. to −8.degree. C. at −5.degree. C./min. After 3 minutes at −8.degree. C., a cotton swab that had been soaked in liquid nitrogen was used to initiate seeding in the manually seeded vial. After an additional 7 minutes at 8.degree. C., specimens were cooled again at −10.degree. C./minute down to −40.degree. C. At −40.degree. C. the rate was increased to −20.degree. C./minute, and at −80.degree. C. samples were plunged into liquid nitrogen ($LN_2$).

Following freezing, the samples were thawed by placing on the bench top (corresponding to .about.300.degree. C./min thawing rate). Once the last of the ice had melted, the glycerol was then diluted drop-wise over a 10-minute period by the addition of PBS; samples were then washed and re-suspended in glycerol-free PBS. Finally, samples were incubated (37.degree. C., humidified atmosphere, 5% $CO_2$, 95% air) for at least one hour prior to evaluation of post thaw count and motility.

The results of this second experiment indicated that samples frozen using the auto-nucleating device of the present invention retained significantly ($p<0.05$) higher motility (66.1.+−.4.7% mean.+−.SEM) than those frozen using manual seeding (56.0.+−.3.8%). Both seeding approaches were significantly higher ($p<0.05$) than the unseeded, negative control samples (43.4.+−.3.7%) as determined using analysis of variance techniques.

In a third experiment it was determined that bound cholesterol would produce no cytotoxic effects on semen cultured over an extended period of time. In this experiment, liquefied semen samples were exposed to culture plates that had been coated with 100.mu.l of the sterol solution. Motility evaluations performed at 1, 2, 4 and 8 hours of incubation showed no significant cytotoxic effect of direct contact with bound cholesterol on human spermatozoa over 8 hours of culture.

Thus, the auto-nucleation device 10 of the present invention is demonstrated to yield better post-thaw motility than using either manual seeding or no seeding in sperm cryopreservation procedures. These experiments demonstrated that sterol-induced ice nucleation is a consistent, reliable method which can reduce supercooling and therefore reduce the associated rapid increase in temperature following the "flash" of ice crystal formation typical of the supercooled solution freezing event with better outcomes. The device and method of the present invention allows the samples to remain in the cooling chamber undisturbed throughout the entire duration of freezing because there is no need for the manual seeding techniques of the prior art.

It is believed that the device and methods of the present invention are particularly suited for standard, commercial sperm banking methods. In a standard commercial sperm bank setting many samples are processed and time/staff constraints do not always allow for controlled rate cooling or for the careful handling that can be achieved in the laboratory. It is believed that the present invention permits repeatable cryopreservation of samples with outcomes that exceed current techniques. In addition, the present invention can enable successful freezing and recovery of samples with low motility that would normally be excluded from donor pools.

Similarly, the device 10 and methods of the present invention may have significant impact on the ability to store cryopreserved hematopoietic stem and/or progenitor cells (PCB HPCs) in a manner that allows for banking and sufficient time for adequate infectious disease screening as well as HLA typing to be performed. Cryopreservation offers the opportunity for preserving PCB derived HPCs from neonatal patients who may benefit from gene therapy, or who are at risk of loosing normal hematopoietic function through disease or iatrogenically via radio- and/or chemotherapy. Recently, increasing efforts have been directed toward refining progenitor cell selection methods. The ability to preserve these relatively "pure" progenitor cell populations (e.g. cells expressing the CD34 surface glycoprotein) potentially minimizes the total volume of the transplanted cell suspension. However, because the volume of PCB typically acquired is much smaller than bone marrow samples, limited numbers of HPCs per kilogram recipient weight can be obtained. This makes efficient and optimal cryopreservation methods for PCB derived HPCs much more critical than in the case of other sources of HPCs (e.g. bone marrow, peripheral blood). The auto-nucleation device of the present invention produces more efficient and optimal means for cryopreservation and recovery of such delicate samples than has heretofore been available. It is believed that integration of the device 10 into ongoing research and development of improved cord blood stem cell cryopreservation methods will result in a unique approach to preserving this cell type with higher recovery with less labor. Experimental protocols have been developed to verify the viability of the device and methods of the present invention in the cryopreservation of PCB and cord blood, as well as bull semen used in commercial artificial insemination facilities. These protocols are described in the above-referenced provisional application No. 60/814,982, which description is incorporated herein by reference.

A further aspect of the present invention recognizes that cryopreservation of various cord blood derived stem/progenitor cells may require completely different procedures and therefore different storage containers than exist under currently known procedures. For banking and storage of multiple cell types derived from umbilical cord blood, it may be optimum to use very different freezing protocols including different cooling/warming rates. Current technology relies either on cryogenic bags, some with multiple chambers, or vials. However both of these systems have substantial drawbacks. The multiple chamber bags do not allow for different cooling rates or CPAs to be used in the different chambers. Vials by themselves cannot be considered "closed" systems at cryogenic temperatures unless a heat sealed over wrap is used, the application of which can compromise sensitive samples.

Figure 3A:
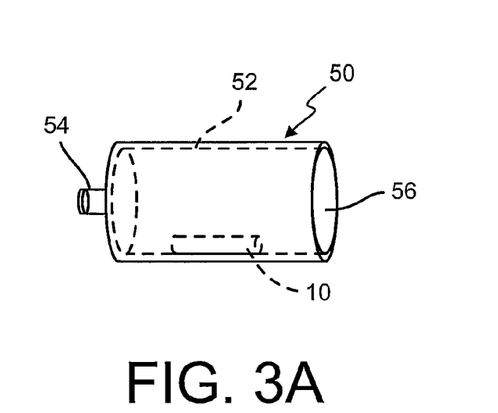
FIG. 3a is a view of a flexible closed system vial for cryopreservation of liquid samples according to a further embodiment of the invention, with the vial shown in an initial condition for delivery of a sample.
Figure 3B:
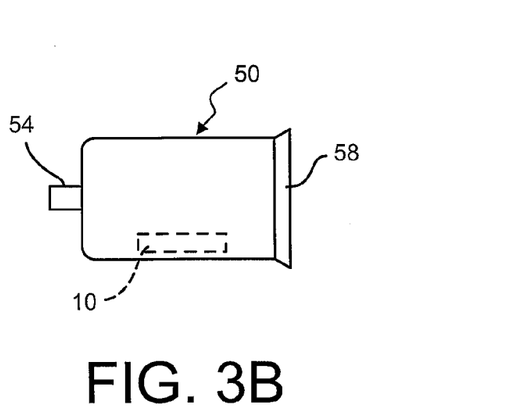
FIG. 3b is a view of the vial shown in FIG. 3a, shown with the vial end sealed.

To overcome this limitation, a further embodiment of the invention resides in a cryopreservation vessel in the form of a flexible closed system vial 50, illustrated in FIGS. 3a, b, which allows the sample to be split between separate units and frozen using different protocols in a closed system. The vial 50 includes a flexible tubular body 52 having a port 54 at one end. The port is sealed, preferably by the same material as the flexible body, but is adapted to be punctured by a needle for aseptically withdrawing the sample after thawing.

As shown in FIG. 3a, the opposite end 56 of the vial is initially open to permit introduction of a liquid sample. Once the vial 50 has been filled, the end 56 is closed, such as by a heat seal strip 58, as shown in FIG. 3b. The closed system vial 50 is then available for freezing and storage of a single unit. Optionally, but preferably, each vial includes the auto-nucleation device 10 described above. As shown in FIG. 3a, the device 10 is preferably adhered to the inner wall of the body 52 so that it is not accessible by a needle passing through the port 52.

It is contemplated that the vial 50 of the present embodiment may be used for multiple freeze/thaw protocols in discrete cryo-containers. Thus, an array of vials 50 may be supported in a fixture with the open end 56 available for introduction of multiple aliquots of the liquid sample. When each vial is filled, the corresponding end is sealed to provide a closed system vial for cryopreservation.

Figure 4:
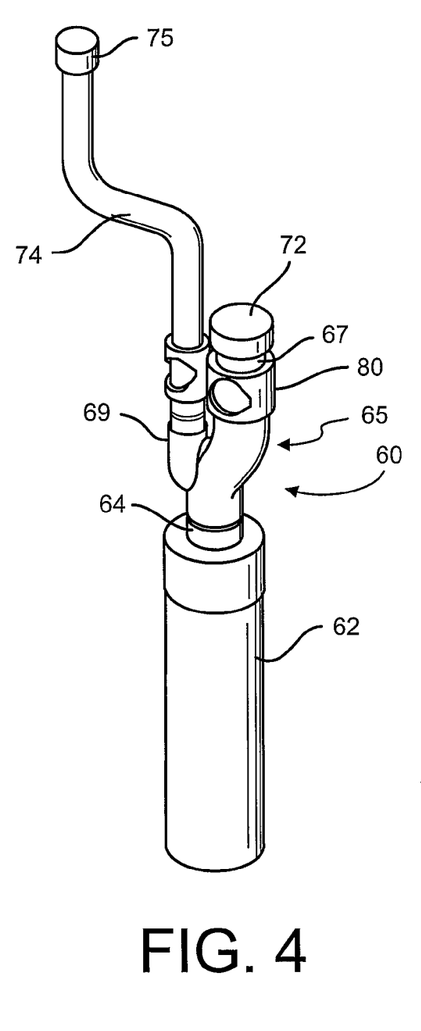
FIG. 4 is a perspective view of a cell cryopreservation device according to another embodiment of the invention.
Figure 5:
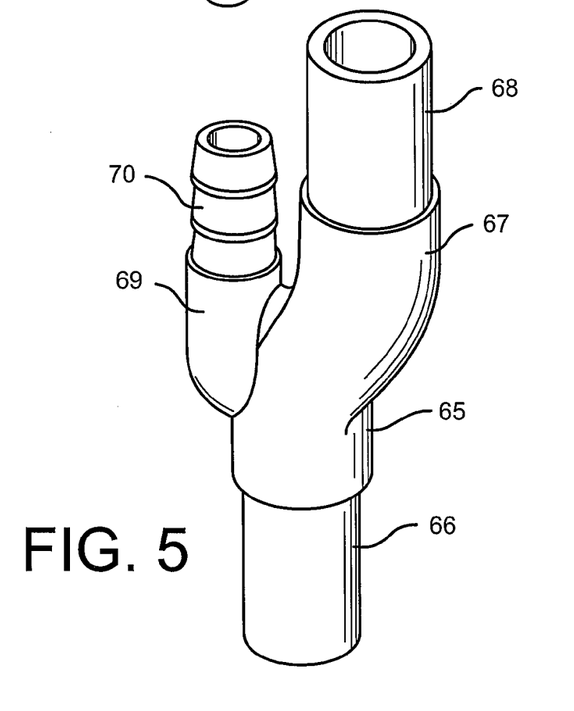
FIG. 5 is a perspective view of an adaptor used in the device shown in FIG. 4.
Figure 6:
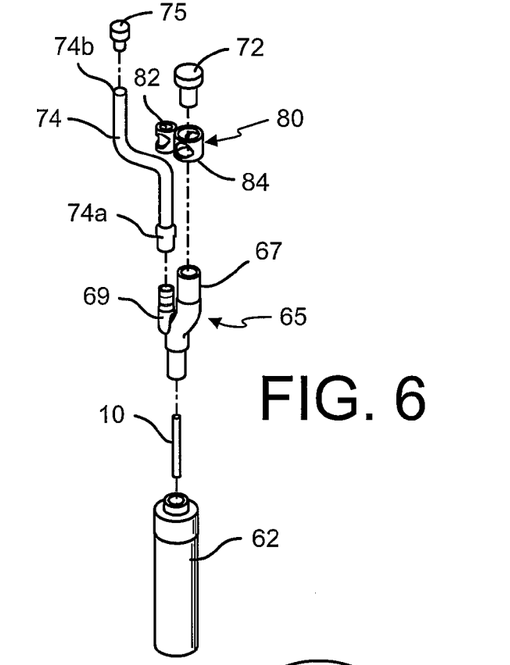
FIG. 6 is an exploded view of the device shown in FIG. 4.

In a further embodiment of the invention, a cryopreservation device 60 is provided, as shown in FIGS. 4-6, that further simplifies the process of obtaining a sample and preparing it for freezing. The device includes a container 62 sized to receive the liquid sample. The container 62 includes an inlet fitting 64 at one end. As shown in FIG. 6, an auto-nucleation device 10 may be introduced into the container through the inlet fitting 64.

The inlet fitting receives an adaptor 65, shown in detail in FIG. 5. The adaptor includes a lower tubular portion 66 that is sized to fit snugly within the inlet fitting 64. The lower portion 66 may be sealed to the inlet fitting using an epoxy or heat sealing, or other suitable means for providing an air and liquid-tight seal between the container 62 and the adaptor 65.

The adaptor includes two tubular branches 67 and 69. The branch 67 terminates in an end portion 68 that is configured to engage a needle septum 72 (FIG. 6). The second branch 69 terminates in a barbed fitting 70. This barbed fitting 70 is in sealed engagement with the end 74a of tubing 74. The free end 74b of the tubing 74 receives its own needle septum 75. Both needle septums 72 and 75 are configured to provide an air and liquid-tight seal at the end of the two branches 67, 69. Moreover, the septums 72, 75 are configured to be pierced by a needle in a known manner and are self-sealing once the needle is removed.

In one specific embodiment, a tubing clip 80 is provided to stabilize the tubing 74 when it is engaged to the adaptor 65. The clip 80 includes a portion 80 configured to slide over the branch 67 of the adaptor and an attached portion 84 that is configured to slide over the tubing 74, as shown in FIG. 4.

The container 62 of the cryopreservation device 60 is sized to be received in the standard "egg carton" separator used to transfer and store cell samples for freezing and eventual thawing. It is contemplated that several such cryopreservation devices 60 carrying cell samples from a common source may be housed in a common egg carton separator. In use, the device 60 is initially stored in the configuration shown in FIG. 4—i.e., with the tubing 74 projecting upward from the cell container itself. The adaptor 65 is sized so that it does not extend beyond the vertical envelope of the container and therefore will not interfere with the storage of other like devices 60. The tubing 74 is shown with a bend that extends outside the vertical envelope. If the devices in the egg carton container are properly aligned, the tubing 74 will not interfere with other cell containers. However, in accordance with the preferred embodiment, it is contemplated that the tubing 74 will be flexible so that it can be arranged as necessary to avoid interfering with other containers 62 in the same egg carton separator.

The tubing 74 is preferably flexible for an additional reason. In particular, the branch 69 and the attached tubing 74 is used for filling the container 62 of the device 60. Thus, in accordance with the present invention, the flexible tubing 74 may be manipulated to permit introduction of a newly extracted cell sample into the container. This introduction occurs in one aspect by piercing the septum 75 with a needle of a syringe containing the extracted liquid sample. Alternatively, the septum 75 may be removable from the end 74b of the flexible tubing so that the sample may be injected directly into the tubing without having to pierce a membrane. In either case, the flexible tubing 74 facilitates this step of filling the container 62 since the tubing can be manipulated as necessary while the container remains in the egg carton container.

Once the sample has been introduced into the container 62 it is contemplated that the branch 69 of the adaptor is permanently sealed. In the preferred embodiment, this sealing occurs by sealing the flexible tubing just above the barbed fitting 70. Once sealed, the remainder of the tubing can be removed since it is no longer needed. In one specific embodiment, a known pinch sealing bar may be used to simultaneously flatten the tubing, heat seal the flattened portion and sever the excess portion. This sealing and cutting preferably occurs as close to the barbed fitting 70 as possible so that no remainder of the flexible tubing 74 will fall outside the vertical envelope of the container 62.

It is desirable that the sealing and cutting steps not compromise the sterile integrity or closed, sealed aspect of the cryopreservation device 60. When the sample is injected through the septum 75 the branch 69 remains sealed throughout the process, even after the needle is removed. Once the branch 69 is sealed the device 60 containing the liquid sample is ready for freezing and storage in the same egg carton that housed the device during the filling step. When it is desired to retrieve the sample, the device 60 may be removed from the egg carton for individual thawing apart from the other devices held in the carton. The needle septum 72 of branch 67 provides the avenue for sterile withdrawal of the sample. Thus, a needle and syringe may be used to pierce the septum and withdraw the liquid sample into the syringe. The empty device 60 may then be discarded.

Figure 7:
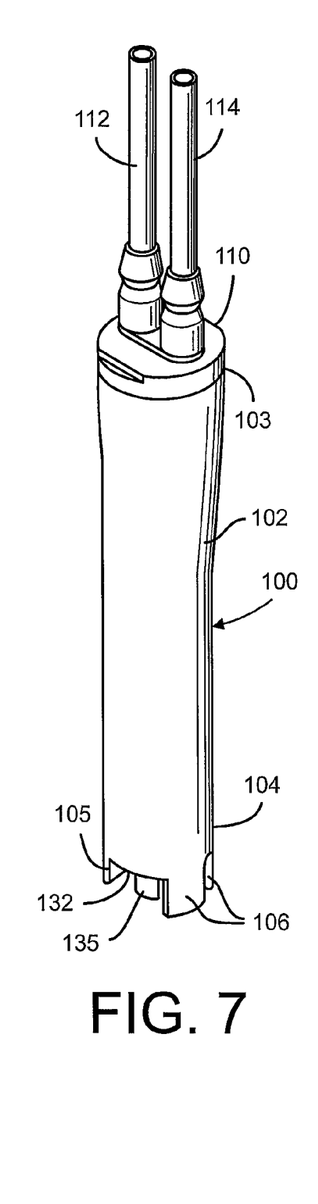
FIG. 7 is a perspective view of a cell cryopreservation device according to a further embodiment.
Figure 8:
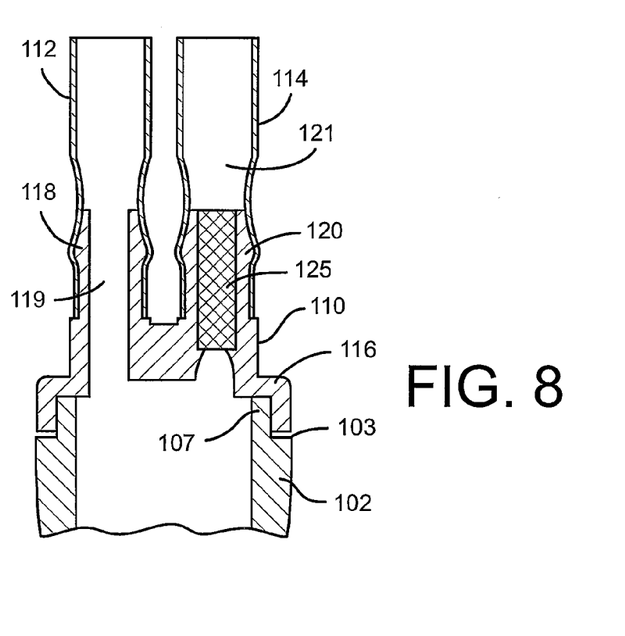
FIG. 8 is a side cross-sectional view of a top portion of the device shown in FIG. 7.
Figure 9:
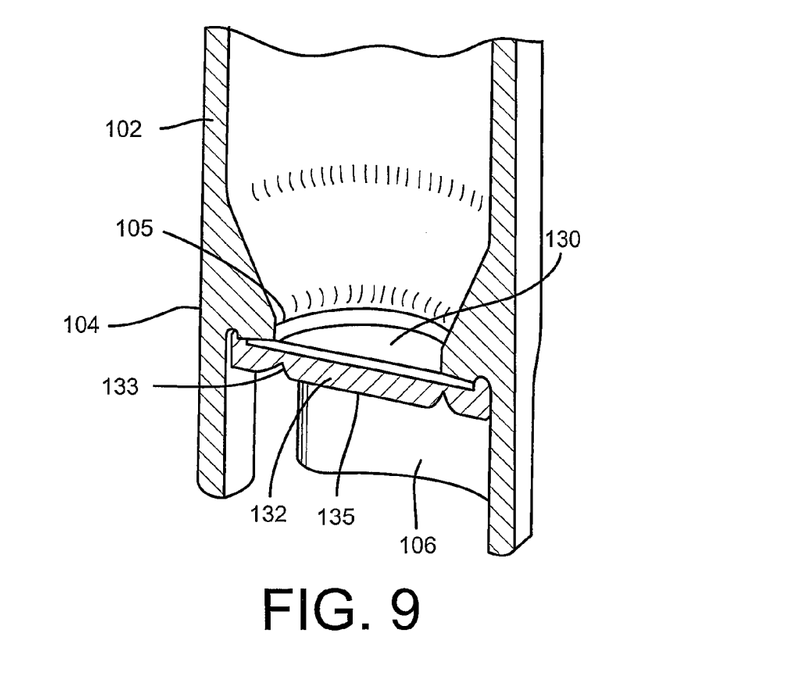
FIG. 9 is a perspective cross-sectional view of a bottom portion of the device shown in FIG. 7.

In an alternative embodiment, a cryopreservation device 100 may be provided as illustrated in FIGS. 7-9. The device includes a container 102 that is similar to the container 62 described above in its capability for cryostorage of a cell suspension, with or without an auto-nucleating device 10 disposed therein. In certain embodiments, the container 100 has a storage volume of 2-5 mL. The container 102 has an open top portion 103 and a bottom portion 104 defining an opening 105. The top portion 103 is hermetically sealed by a cap 110, as shown in the cross-sectional view of FIG. 8. The top portion defines an annular flange 107 over which is mounted a lower skirt 116 of the cap 110. This lower skirt is preferably heat sealed to the annular flange in conventional manner to form a fluid-tight joint capable of withstanding cryogenic temperatures.

The cap 110 supports an inlet branch 112 and a vent branch 114, each of which may be in the form of sterile tubing. The inlet branch 112 may be provided with a standard needle septum, such as the septum 75 described above. The two branches 112, 114 are mounted over corresponding fittings 118, 120, with each fitting defining a passageway 119, 121 in communication with the interior of the container 112. Each branch is hermetically sealed over the corresponding fitting, again to form a fluid-tight cryogenic-capable joint.

In the embodiment of FIGS. 7-9, the branch 114 serves as a vent branch, rather than as an outlet branch as in the previous device 60. A filter element 125 may be disposed within the passageway 121 of the fitting 120. In a preferred embodiment, this filter element is a 3.mu.m sterile microfilter. The micro-filter 125 is gas permeable but generally impermeable to the liquid sample or cell suspension being stored within the container.

In the present embodiment, the device 100 provides for removal of the stored suspension through the bottom portion 104 of the container 102, rather than through the cap as in the prior embodiment. Thus, as shown in the cross-sectional view of FIG. 9, the opening 105 in the container is sealed by a needle septum 130. The outlet septum 130 is suitably hermetically sealed to the container 102, such as by heat sealing. To protect the septum, a removable cover 132 may be provided that is affixed to the container around the septum. The cover 132 may define a tear portion 133 in the form of a thinner or weakened region that allows the central portion 135 of the cover to be removed. A tab 135 may be provided, as shown in FIG. 7, to facilitate removal of the central portion 135. The cover may be a foil film that is adhered around its perimeter to the bottom portion 104 of the container 102.

The manner of use of the cryopreservation device 100 is similar to the device 60 described above. In particular, a cell suspension is introduced into the container 102 through the inlet branch 112, and particularly through the needle septum described above. Alternatively, the inlet branch may be provided with a standard needle or needle-less port. As the cell suspension is injected into the container, the air within is vented through the filter 125 in the vent branch 114. In certain embodiments, the micro-filter 125 is configured to be generally impermeable to the cell suspension. Thus, once the level of the suspension within the container reaches the filter 125 the suspension will not pass through the filter and the increase in pressure will terminate the flow of liquid into the container.

Once the container 102 is filled the two branches may be heat sealed, using for instance the heated pinch sealer described above, so that the container is completely and hermetically sealed. Of course it is understood that the needle septum 130 and cover 132 remain intact as the container 102 is filled. The filled and sealed device 100 can then be cryogenically stored.

When it is desired to withdraw the cell suspension, the device and contents are first thawed in a known manner. Once thawed, the cover 132 is removed to expose the septum 130. The vent branch 113 is severed to open the vent passageway 121. The cell suspension may then be withdrawn by a syringe or similar device puncturing the septum 130. The bottom portion 104 of the container may define a series of prongs 106 that are adapted to engage the withdrawal device or syringe. In some embodiments the prongs 106 are configured for docking the withdrawal device, while in other embodiments the prongs may be provided with LUER threads for engaging the LUER fitting on the withdrawal syringe.

Figure 10:
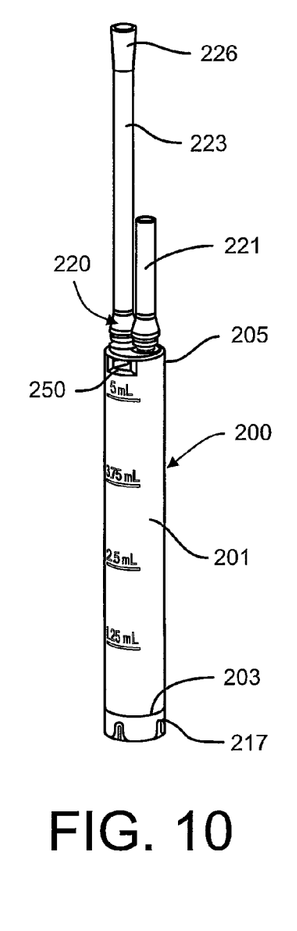
FIG. 10 is a perspective view of a cryopreservation device according to another embodiment.
Figure 12:
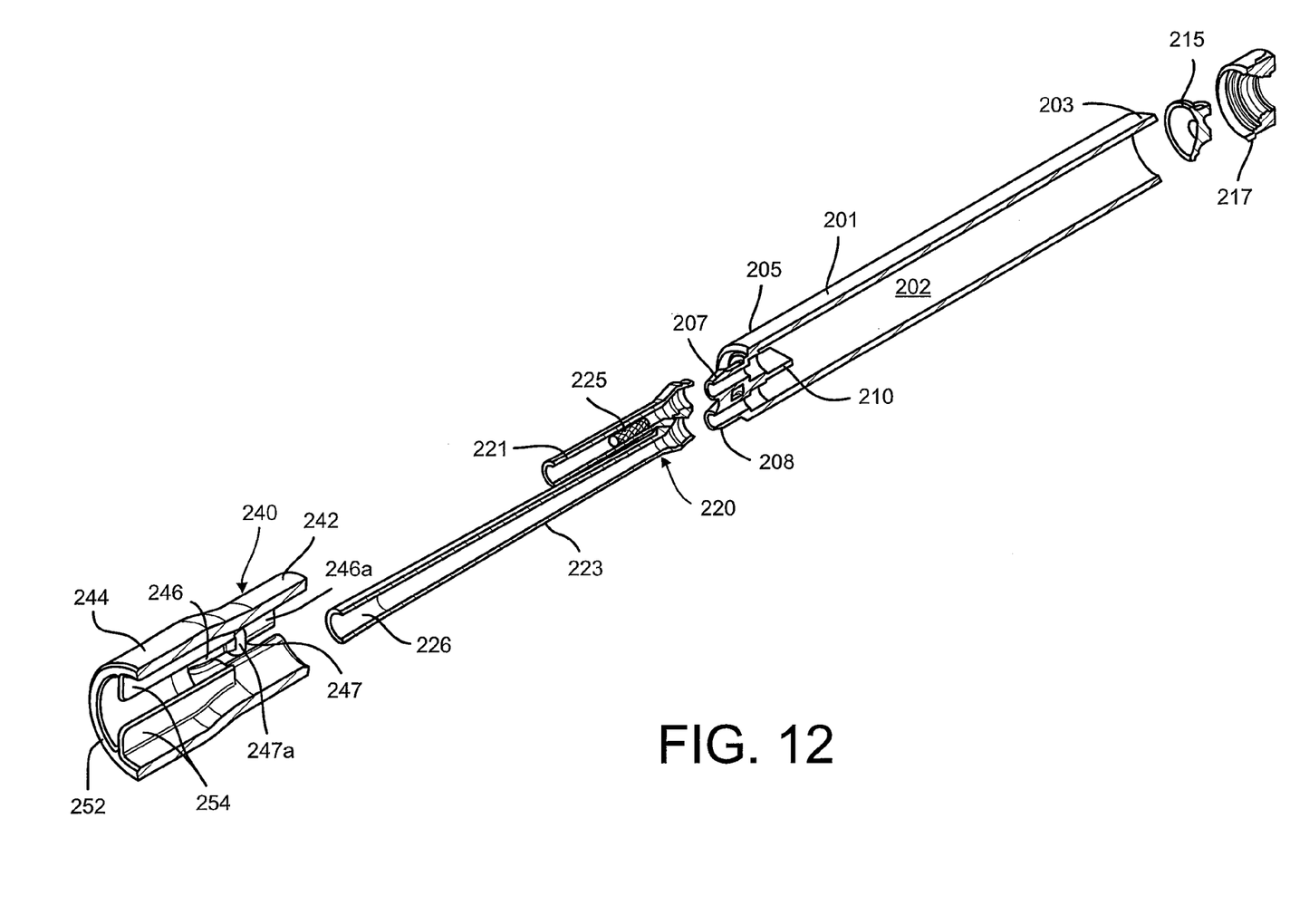
FIG. 12 is an exploded cross-sectional view of the device and support cap shown in FIG. 11.

According to a further embodiment, a cryopreservation vessel 200 includes a container or vial 201 that may be graduated, as shown in FIG. 10. The vessel 200 has an open lower end 203 and a closed upper end 205. As seen in FIG. 12, the container 201 is essentially a one-piece body forming a hollow interior 202 from the open lower end 203. At the closed upper end 205 the one-piece body is configured to form a pair of tube adapters 207, 208 opening into the hollow interior 202. The openings of the two tube adapters into the interior are separated by a wall 210. As with the prior embodiments, the adapter 207 may be connected to a vent, while the adapter 208 may be connected to a source of fluid to be cryogenically preserved within the vessel 200. The wall 210 prevents fluid entering through the adapter 208 being immediately drawn out the adapter 207, particularly when a negative pressure is applied to the adapter 207, as described herein.

The open end 203 of the container 201 is closed by a needle septum 215, which can be configured and function like the needle septum 130 discussed above. The needle septum 215 is retained by a cover 217 that is sealed to the open end 203 of the container in a conventional manner to provide a leak-proof seal.

The vessel 200 further includes an adapter body 220 that includes a vent tube 221 and an inlet tube 223. The ends of the tubes are mounted over the corresponding fittings 207, 208 in a suitable manner to provide a permanent, leak-proof sealed engagement. The vent tube 221 may preferably include a filter element 225 lodged within the tube, similar to the filter 125 described above. The inlet tube 223 may include a flared end 226 for engagement with a tube adapter, as described herein.

Figure 11:
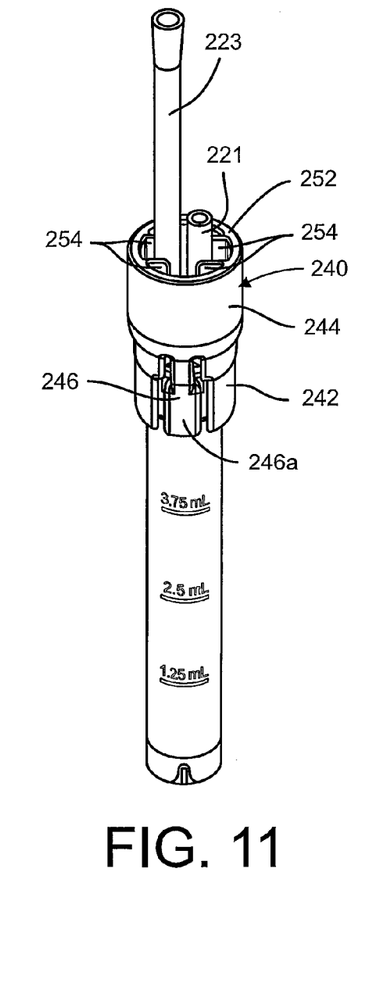
FIG. 11 is a perspective view of the cryopreservation device of FIG. 10 with a support cap mounted thereon according to a further feature disclosed herein.
Figure 13:
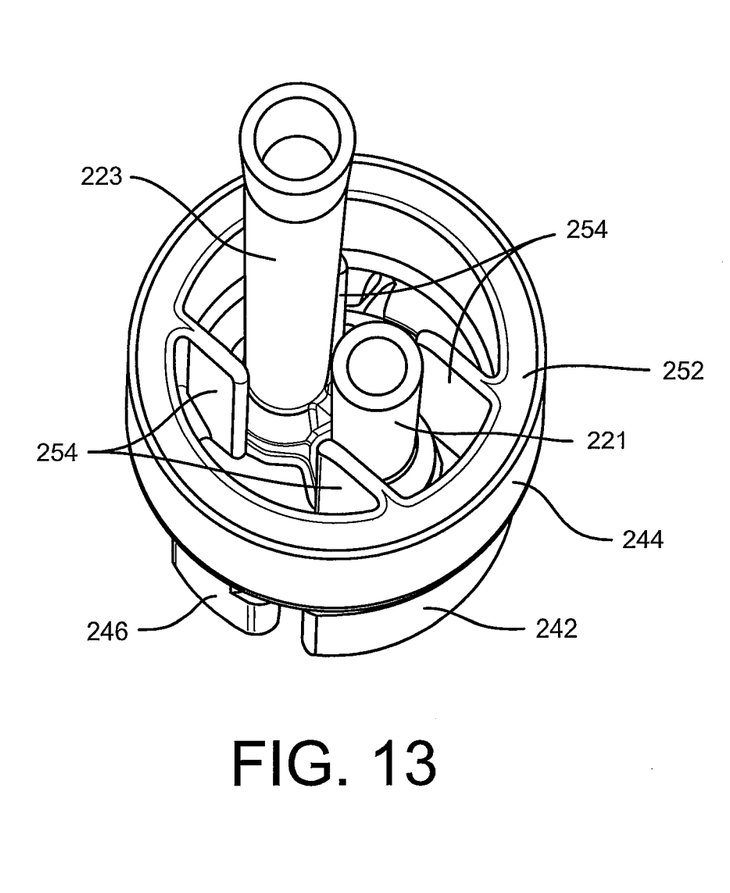
FIG. 13 is an enlarged to perspective view of the top of the device and support cap shown in FIGS. 11-12.

As thus far described, the vessel 200 is similar to the vessel 100. However, the container 201 is modified to accommodate a support cap 240, as shown in FIGS. 11-13. The support cap 240 includes a lower portion 242 and an upper portion 244, both of generally cylindrical configuration and sized for a snug fit over the container 201. The lower portion 242 includes at least two prongs 246 with inwardly directed tabs 247. The tabs 247 are sized and arranged to lock within corresponding recesses 250 formed in the container 201 (FIG. 10). The tabs 247 are inwardly directed so that the tabs must be moved outwardly by deflecting the prongs 246 as the cap 240 is slid over the container. The tabs include an angled upper surface 247a that allows the tabs to be smoothly pulled out of the recess 250 when it is desired to remove the cap. The tabs 247 are arranged in the middle portion of the prongs 246 so that a lower part 246a of the prongs extends below the tabs for manual engagement to release the tabs from the recesses. The lower part 246a provides leverage to facilitate release of the tabs while also protecting the tabs from dislodgement by accidental contact.

The upper portion 244 of the cap 240 is configured to protect the tubes 221 and 223 extending from the top of the container. Thus, the upper portion 244 includes a circumferential wall 252 with internal walls 254 arranged to flank the sides of the tubes, as best seen in FIG. 13. The walls thus prevent bending of the tubes at their union with the adapters 207, 208 of the vessel 200, which prevents breaking the fluid-tight seal and contaminating the contents.

Figure 14:
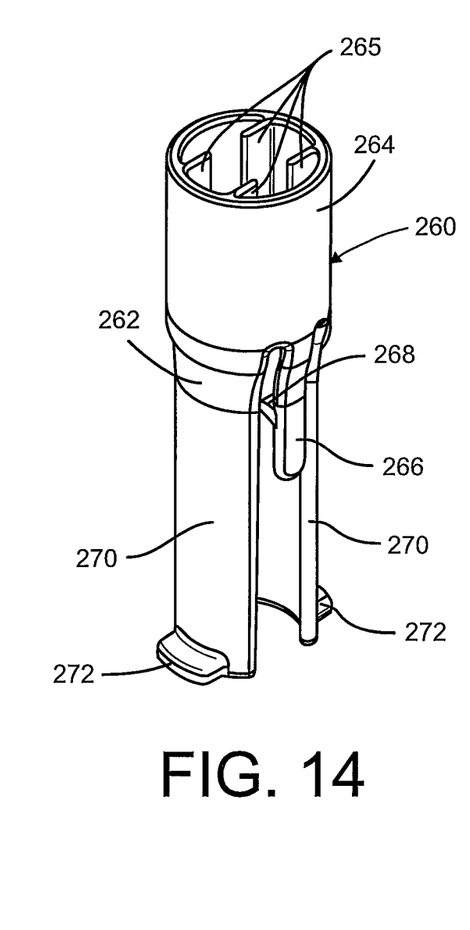
FIG. 14 is a perspective view of a support cap according to an alternative embodiment.

A modified cap 260 is illustrated in FIG. 14. This cap is particularly configured to support the cryopreservation vessel 200 in a centrifuge or other instrument. In some instances it is desirable to centrifuge the contents of the vessel 200, such as to separate cell pellet from supernatant. The container 201 may not be easily mounted within a centrifuge, so the modified cap 260 provides additional support for the container. In particular, the cap 260 includes a lower portion 262 and an upper portion 264. The upper portion 264 may be configured like the upper portion 244 of the cap 240, complete with internal walls 265 to protect the tubing.

In addition, like the cap 240, the lower portion 262 of the cap 260 includes at least two prongs 266 with tabs 268 configured to engage the recesses 250 in the container 201. However, the lower portion 262 includes legs 270 that extend beyond the end of the prongs 266. Furthermore, these legs 270 terminate in outward projecting tabs 272. The legs 270 thus extend along a significant portion of the length of the container 201 from the recesses 250. The outward tabs 272 are configured to engage recesses or mounting features of an instrument, such as the centrifuge discussed above. Not only do the longer legs 270 provide support for the container, the legs and particularly the tabs 272 provide a mechanism for releasably engaging the instrument to fully support the cryopreservation vessel 200 within the instrument.

Figure 15A:
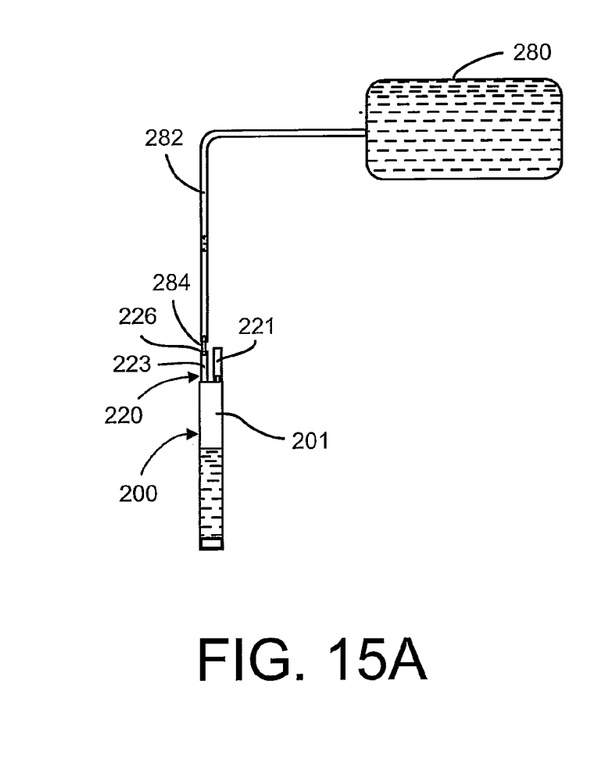
FIGS. 15a, 15b are schematic representations of the cryopreservation device of FIG. 10 according to two uses.
Figure 15B:
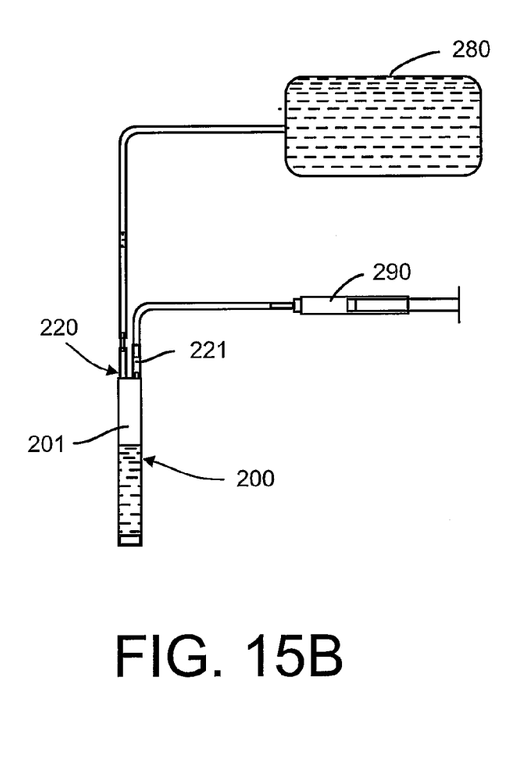

Uses of the vessel 200 are depicted in FIGS. 15a, 15b. In both uses, the container is coupled to a source of fluid, such as a blood bag 280. The blood bag includes a tube 282 that is coupled to the inlet branch 223 of the adapter body 220. In one embodiment, an adapter 284 may be engaged between the flared end 226 of the inlet branch and the blood bag tube 282. In one approach shown in FIG. 15a, the blood is gravity fed into the container 201 with air escaping through the vent branch 221. In another approach, shown in FIG. 15b, the entire system is closed, with a syringe 290 coupled to the vent branch 221. The syringe is withdrawn to apply a negative pressure to the container 201 to thereby draw blood from the bag 280 into the container.

Figure 16:
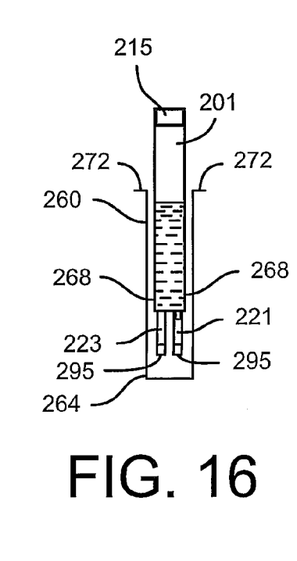
FIG. 16 is a schematic representation of the cryopreservation device and support cap of FIG. 14 according to one use thereof.

Once the blood or other fluid to be cryopreserved has been drawn into the container, the tubing is severed and sealed, as shown in FIG. 16. The ends 295 of the sealed tubes are cut to reside below the end of the upper portion 264 of the cap 260 when the cap is engaged to the container 201. Thus, as shown in FIG. 16, the ends of the tubes are completely enclosed and protected. The tabs 272 of the cap 260 are available to mount the vessel 200 within a centrifuge or other vessel. It can further be appreciated that the cap 260 acts as a support stand to support the vessel with the needle septum 215 facing upward. When the contents of the container are centrifuged, the supernatant will naturally migrate upward where it can be easily accessed and drawn off by a needle through the septum. Once the supernatant has been removed, the cap 260 can be removed from the container 201 and the contents can then be cryogenically preserved.

It can be further appreciated that the procedures depicted in FIGS. 15a-15c may be utilized without subsequent cryopreservation. For instance, current blood testing requirements for blood banking according to American Association of Blood Banks (AABB) standards dictate destruction of a blood unit that has been tested because there is currently no means to effectively remove aliquots of blood into testing containers or without potential contamination of the entire unit. This requirement results in the destruction of about one percent of the blood units processed by all blood banks, which can be significant in terms of cost and blood shortages. The testing container must allow centrifugation for cell pelleting while retaining a closed system to avoid contamination.

The vessel 200 satisfies the AABB standards so that blood banking or medical practitioners can withdraw blood samples directly from units of blood without compromising the remainder of the blood unit. Once the blood sample has been withdrawn from the blood bag 280 into the container 201 the blood bag tube 282 can be sealed and disconnected from the adapter 284, thereby preserving the unit of blood in the blood bag 280. The blood sample within the container 201 can then be mounted within the cap 260 to be transported to a laboratory and centrifuged. The needle septum 215 permits sterile withdrawal of the supernatant for further analysis, such as to determine cell counts, or to detect the presence of hemoglobin or microorganisms in the blood sample.

It is contemplated in some embodiments that the containers 62, 102 and 201 of the cryopreservation vessels 60, 100 and 200 may be provided with an initial vacuum. This vacuum assists withdrawal of the liquid sample during the step of filling the vessel containers. Since the openings to each branch 67/69, 112/114 and 221/223 are sealed (either by the corresponding septums 72, 75 or by heat-sealing), the vacuum may be maintained over a long period of time. A cap may be provided over each branch to ensure an air-tight seal. In a specific embodiment, the initial vacuum in the containers 62, 100 and 201 may be at a sub-atmospheric pressure of between 100 mmHg (absolute) and about 160 mmHg (absolute).

The cryopreservation vessels 60, 100 and 200 may be formed of standard materials used in the field of blood banking and long-term storage in standard cryogenic conditions (i.e., temperatures as low as −196.degree. C.). Current O.S.H.A. recommendations are to make the components of a suitable plastic to achieve compliance with certain blood borne pathogen standards and other mandates. Thus, the containers, fittings and tubings of each of the embodiments disclosed above may be formed of a suitable plastic, such as polystyrene or polypropylene. In order to fit in standard egg carton containers, the vessels (after sealing of the flexible tubing) should fit within a 10 mm diameter and a 90 mm height. The flexible tubing 74 must also be capable of withstanding cryogenic temperatures without compromising the ability to heat seal and sever the tubing when sealing the branch 69 of the adaptor 65. In one specific embodiment, the flexible tube is formed of TYGON® or a similar material.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A cryopreservation device comprising:
a container for receiving and storing a liquid sample under cryopreservation conditions, said container having a hollow interior, and an outlet opening;
a first tube fluidly communicating with said hollow interior, said first tube defining a vent passageway;
a filter element disposed within said vent passageway;
a second tube fluidly communicating with said hollow interior, said second tube defining an inlet passageway between a first end opening into said hollow interior and a sealed second end, and wherein said second tube is configured for connection to a source of liquid to be cryogenically preserved; and
a needle septum sealing said outlet opening, said needle septum configured for removal of a stored liquid through a needle, and wherein said container is hermetically sealed.

2. The cryopreservation device of claim 1, wherein said second tube comprises heat-sealable sterile tubing.

3. The cryopreservation device of claim 2, wherein said second tube further comprises an input needle septum at said sealed second end.

4. The cryopreservation device of claim 2, wherein said second tube further comprises a needle-less port at said sealed second end.

5. The cryopreservation device of claim 2, wherein said second tube further comprises a heat sealed portion at said sealed second end.

6. The cryopreservation device of claim 1, wherein said filter element is gas permeable but generally liquid impermeable.

7. The cryopreservation device of claim 1, wherein said filter element is a sterile micro-filter.

8. The cryopreservation device of claim 1, further comprising a removable septum cover.

9. The cryopreservation device of claim 8, wherein said removable septum cover comprises a foil film.

10. The cryopreservation device of claim 1, wherein said container has a storage volume of 2-5 mL.

11. The cryopreservation device of claim 1, further comprising a cryoprotectant received within said container.

12. The cryopreservation device of claim 1, wherein said device is comprised of materials suitable to remain hermetically sealed at cryopreservation conditions at a temperature as low as −196° C.

13. A method of cryogenically storing a sample, said method comprising:
introducing a liquid sample into a cryopreservation device as described in claim 1; and
storing said device at cryopreservation conditions at a temperature as low as −196° C.

14. A sample container device comprising:
a container for receiving a sample, said container comprising an elongated body, said body defining a hollow interior from an open end and being closed at the opposite end by an inlet tube fitting and a vent tube fitting opening to said hollow interior;
a gas permeable sterile micro-filter received in said vent tube fitting;
a needle septum closing said open end; and
a length of heat sealable tubing coupled to said inlet fitting, wherein the flexible tubing is comprised of material suitable to form a heat seal that withstands cryopreservation conditions at temperature as low as −196° C. without compromising the heat seal, and wherein said heat sealable tubing is sealed.

15. The device of claim 14, further comprising a needle septum sealing said heat sealable tubing.

16. The device of claim 14, further comprising a removable septum cover.

17. The device of claim 16, wherein said removable septum cover comprises a foil film.

18. The device of claim 14, further comprising a cryoprotectant received within said container.

19. The device of claim 14, wherein said device is hermetically sealed.

20. The device of claim 14, wherein said device is comprised of materials suitable to remain hermetically sealed at cryopreservation conditions at a temperature as low as −196° C.

21. The cryopreservation device of claim 14, further comprising a needle-less port sealing said heat sealable tubing.

22. The cryopreservation device of claim 14, further comprising a heat sealed portion sealing said heat sealable tubing.

* * * * *